(12) United States Patent
Nakamura et al.

(10) Patent No.: US 8,522,617 B2
(45) Date of Patent: Sep. 3, 2013

(54) KNEE ACOUSTIC MATCHING DEVICE FOR ULTRASONIC PROBE

(75) Inventors: Kozo Nakamura, Tokyo (JP); Isao Onishi, Tokyo (JP); Satoru Ohashi, Tokyo (JP); Eiichi Minagawa, Mitaka (JP); Koji Hirota, Mitaka (JP); Ryoichi Sakai, Mitaka (JP); Koji Ogawa, Mitaka (JP); Koichi Miyasaka, Mitaka (JP); Masaru Murashita, Mitaka (JP)

(73) Assignees: The University of Tokyo, Tokyo (JP); Hitachi Aloka Medical, Ltd., Tokyo (JP)

( * ) Notice: Subject to any disclaimer, the term of this patent is extended or adjusted under 35 U.S.C. 154(b) by 349 days.

(21) Appl. No.: 13/055,415

(22) PCT Filed: Jul. 17, 2009

(86) PCT No.: PCT/JP2009/062997
§ 371 (c)(1),
(2), (4) Date: Jan. 21, 2011

(87) PCT Pub. No.: WO2010/010856
PCT Pub. Date: Jan. 28, 2010

(65) Prior Publication Data
US 2011/0126629 A1    Jun. 2, 2011

(30) Foreign Application Priority Data

Jul. 22, 2008  (JP) ................................ 2008-188727

(51) Int. Cl.
*G01N 29/00*   (2006.01)

(52) U.S. Cl.
USPC .......................................................... 73/644

(58) Field of Classification Search
USPC ..................................... 73/644; 600/438, 443
See application file for complete search history.

(56) References Cited

U.S. PATENT DOCUMENTS

| | | | | |
|---|---|---|---|---|
| 4,688,578 | A | * | 8/1987 | Takano et al. ................. 600/459 |
| 5,178,135 | A | * | 1/1993 | Uchiyama et al. ................ 601/4 |
| 5,485,839 | A | * | 1/1996 | Aida et al. .................... 600/427 |
| 5,730,135 | A | | 3/1998 | Otani et al. |

(Continued)

FOREIGN PATENT DOCUMENTS

| | | |
|---|---|---|
| EP | 0800788 A1 | 10/1997 |
| JP | 8-280677 A | 10/1996 |

(Continued)

OTHER PUBLICATIONS

European Search Report dated Dec. 19, 2011, issued in corresponding European Patent Application No. 09800370.0.

(Continued)

*Primary Examiner* — J M Saint Surin
(74) *Attorney, Agent, or Firm* — Westerman, Hattori, Daniels & Adrian, LLP

(57) ABSTRACT

An acoustic matching device has a water bag (64) that contains water and a water bag support frame (66) that sandwiches and supports the water bag on the left and right sides of the knee and curves along the knee cap. The water bag becomes a plate shape curved along the shape of the water bag support frame, which touches the knee cap and fits the unevenness of the knee. When an ultrasonic probe is moved along the knee cap, the acoustic matching between the knee cap and the ultrasonic probe is obtained.

3 Claims, 13 Drawing Sheets

(56) References Cited

U.S. PATENT DOCUMENTS

| | | | |
|---|---|---|---|
| 6,295,365 B1* | 9/2001 | Ota | 381/114 |
| 7,204,807 B2* | 4/2007 | Tsoref | 600/438 |
| 2007/0066897 A1 | 3/2007 | Sekins et al. | |
| 2009/0005710 A1* | 1/2009 | Min et al. | 601/2 |
| 2012/0271294 A1* | 10/2012 | Barthe et al. | 606/28 |
| 2013/0023884 A1* | 1/2013 | Fitz et al. | 606/88 |

FOREIGN PATENT DOCUMENTS

| | | |
|---|---|---|
| JP | 9-234200 A | 9/1997 |
| JP | 2002-345821 A | 12/2002 |
| JP | 2009-045189 A | 3/2009 |

OTHER PUBLICATIONS

Notification Concerning Transmittal of International Preliminary Report on Patentability (Forms PCT/IB/373) of International Application No. PCT/JP2009/062997 issued date Feb. 3, 2011 with Forms PCT/ISA/237 and PCT/IB/326.

International Search Report of PCT/JP2009/062997, mailing date Aug. 25, 2009.

Notification of Transmittal of Translation of the International Preliminary Report on Patentability (Form PCT/IB/338) of International Application No. PCT/JP2009/062997 mailed Mar. 17, 2011 with Forms PCT/IB/337 and PCT/ISA/237.

* cited by examiner

KNEE ACOUSTIC MATCHING DEVICE FOR ULTRASONIC PROBE

TECHNICAL FIELD

The present invention relates to an acoustic matching device which is used for ultrasound diagnosis of cartilage of the knee.

BACKGROUND ART

Gonarthrosis is a disorder in which wear of cartilage which functions as a cushion of the knee joint causes inflammation or deformation of the knee joint, resulting in pain. The number of patients suffering gonarthrosis increases with age. However, if the thickness and surface shape of the cartilage of the femur can be accurately known before the condition reaches a crisis, a preventive action can be taken. With the population increase of the elderly, the number of gonarthrosis patients is currently expected to increase, and a simple diagnosis method is desired.

Known methods of diagnosing gonarthrosis include a method in which an arthroscope (endoscope) is inserted into the knee and a state of the surface of the cartilage is observed, and a method in which gonarthrosis is estimated based on the degree of opening of a gap in the joint through X-ray examination. However, these diagnosis methods cannot measure the thickness of the cartilage or obtain a three-dimensional shape of the cartilage.

In consideration of this, Patent Literature 1 discloses a system wherein an in-joint probe is inserted into the knee joint and ultrasound is transmitted and received, to evaluate the thickness of the cartilage of the knee joint. However, because this system is invasive, the system cannot be easily used. Therefore, this system is not suited for examination of many examinees such as a periodical medical examination.

An MRI (Magnetic Resonance Imaging) device is a non-invasive image diagnosis device, can in principle image the cartilage distinguished from the bone, muscle, body fluids, etc., and can measure the thickness of the cartilage. However, the usage cost for MRI is high and the measurement requires a long time, and thus, the MRI is not suited for use in examination of many examinees.

RELATED ART REFERENCES

Patent Literature

Patent Literature 1: JP 2002-345821 A

DISCLOSURE OF INVENTION

Problem to be Solved

In the diagnosis by ultrasound, ultrasound is transmitted to and received from a surface of the body, and the shape of the internal tissues such as organs and bones can be obtained based on the received ultrasound echo. With regard to the knee cartilage also, this characteristic can be taken advantage of, and a non-invasive and simple diagnostic device can be provided. In this process, an ultrasonic probe which transmits and receives ultrasound to and from the body surface must be positioned at a suitable position for measuring the shape of the knee cartilage, and must be moved in a suitable path for scanning (mechanical scanning). In addition, an acoustic matching member which corresponds to such scanning of the ultrasonic probe and which can be adapted to the shape of the knee surface is required.

The present invention advantageously provides an acoustic matching device which corresponds to the movement of the ultrasonic probe which transmits and receives ultrasound to and from a knee in a bent state and which is adapted to the shape of the knee surface.

Means for Solving the Problem

According to one aspect of the present invention, there is provided an acoustic matching device which executes acoustic matching by being interposed between a knee cap having an uneven surface and an ultrasonic probe which moves along the knee cap. A water bag containing water is employed as an acoustic matching layer, and a water bag support frame is provided which sandwiches and supports the water bag at a left side and a right side of the knee when the device is mounted on the knee and which is curved along the knee cap. The water bag has a plate shape which is curved according to the shape of the water bag support frame, and fits the shape of the knee cap by virtue of the flexibility of the water bag itself.

According to another aspect of the present invention, preferably, in the acoustic matching device, the water bag comprises a fixed portion having a side supported by the water bag support frame and having a defined outline shape, and a free portion which extends from the fixed portion toward a distal side and which is allowed to move in a front and rear direction of the knee. Provision of the free portion secures ease of mounting of the acoustic matching device to the knee and a wide measurement range when the acoustic matching device is mounted.

According to another aspect of the present invention, preferably, in the acoustic matching device, an edge on a distal side of the free portion of the water bag is sandwiched by a distal side frame which extends in a left and right direction. With the distal side frame, the free portion is maintained in a plate shape.

According to another aspect of the present invention, preferably, in the acoustic matching device, there is provided a flexible frame having a thin plate shape which extends from the water bag support frame toward the distal side and which is connected to the distal side frame. The flexible frame supports the weight of the free portion of the water bag and the weight of the distal side frame, and prevents deformation of the free portion exceeding the necessary deformation. In addition, the thin plate has a width direction aligned with the left and right direction, and is deflected to restrict movement of the distal side frame in the left and right direction while allowing movement of the distal side frame in the front and rear direction. The movement of the water bag can be limited, and handling of the water bag can be facilitated.

Advantages

According to various aspects of the present invention, there is provided a device which is interposed between the ultrasonic probe which moves along the knee cap and the knee cap having an uneven surface, and which can achieve superior acoustic matching.

BEST MODE FOR CARRYING OUT THE INVENTION

Figure 1:
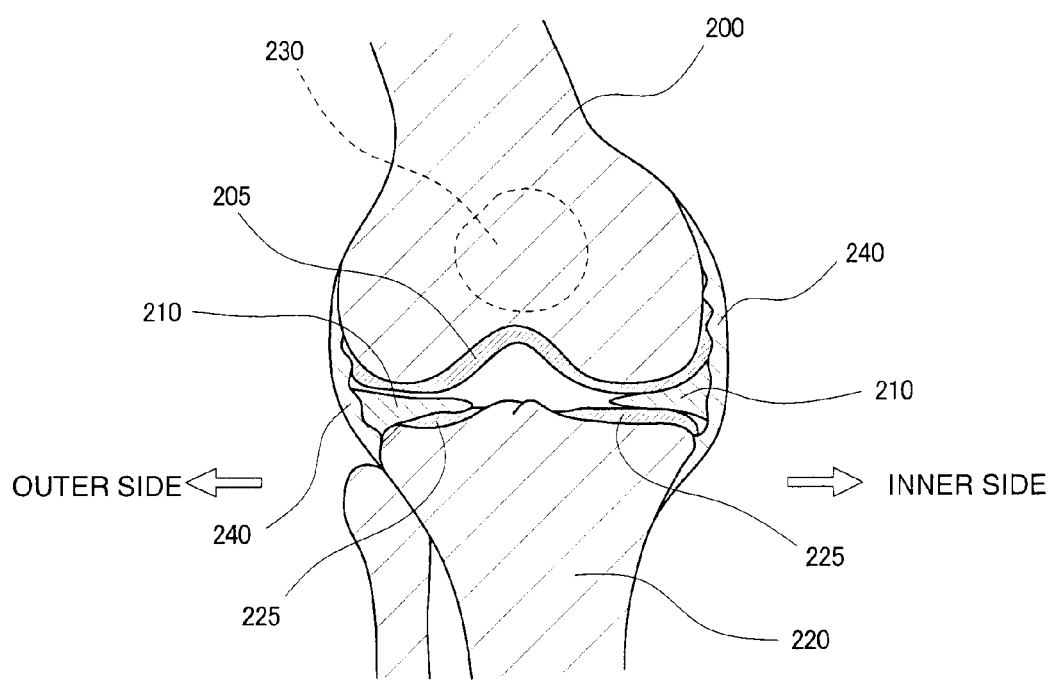
FIG. 1 is a schematic cross sectional diagram for explaining the structure of the knee joint.

Prior to the description of an example device structure of a preferred embodiment of the present invention, an internal structure of a knee joint (in particular, a human knee joint) to which the device is applied will first be briefly described with reference to FIG. 1. FIG. 1 is a schematic cross sectional diagram of a knee joint of the right leg in a standing posture, as viewed from the front side of the body.

As shown in FIG. 1, the knee joint comprises a distal end portion of a femur 200, a proximal end portion of a tibia 220, and a patella 230. A surface of a distal end of the femur 200 is covered with cartilage 205, and a surface of the proximal end of the tibia 220 is covered with cartilage 225. Of the surface of a bone (for example, the femur 200), the portion covered with cartilage is called a subcartilaginous bone. A meniscus 210 is present between the cartilage 205 of the femur 200 and the cartilage 225 of the tibia 220. The distal end of the femur 200 projects in two branches (which are called the medial condyle and the lateral condyle, respectively) as shown in the figures, when viewed from the front direction of the body in a standing posture, and the cartilage 205 of the medial condyle and the cartilage 205 of the lateral condyles are in contact with the cartilage 225 on the proximal end of the tibia 220 via holes formed in the medial and lateral meniscuses 210. The knee joint portion as described above is covered with synovium and a capsular ligament 240.

The cartilage 205 on the distal end of the femur 200 widely covers the surface of the distal end portion, and a portion of the cartilage 205 which contacts the cartilage 225 on the proximal end of the tibia 220 at the standing posture is a portion where the load of the upper body is strongly applied. This portion is called a cartilage load portion. The cartilage load portion tends to be worn, and, when the wear becomes significant, gonarthrosis is caused. For diagnosing gonarthrosis, the thickness of the cartilage of the cartilage load portion is an important judgment criterion.

The thickness of the cartilage 205 on the distal end of the femur 200 of a human is thin and is approximately 2 mm~3 mm for a healthy person. Therefore, in order to measure the thickness with high precision with the method of ultrasound diagnosis, an ultrasound beam is desirably applied at an angle which is as close to perpendicular as possible with respect to the surface of the cartilage 205. However, in the standing posture, because the cartilage load portion on the distal end of the femur 200 is in contact with the cartilage 225 of the tibia 220, if the ultrasound beam is to be applied at an angle close to perpendicular with respect to the surface of the cartilage load portion in this state, the ultrasound beam must be applied from the side of the tibia toward an upward direction. However, application of the ultrasonic probe in such a position is not possible. Even if the ultrasonic probe can be placed on such a position, the cartilage would be in shadow of the femur or tibia, and, thus, the ultrasound tends not to reach the cartilage and consequently the cartilage cannot be imaged.

Figure 2:
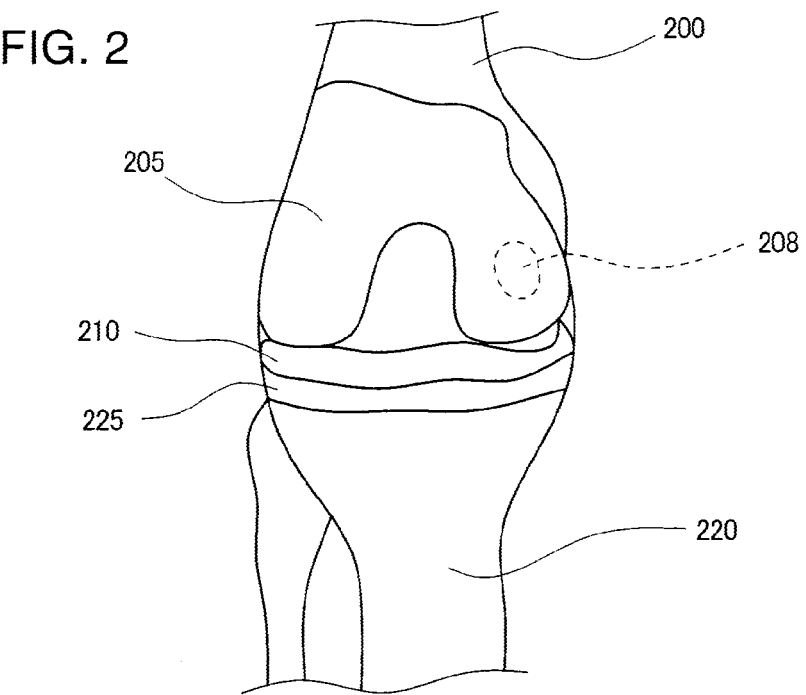
FIG. 2 is a diagram showing the knee joint at a sitting position, as viewed from the front.

On the other hand, when the knee is significantly bent (for example, to approximately 90°) such as, for example, when the person is sitting on a chair, as shown in FIG. 2, a load portion 208 of the cartilage 205 on the distal end of the femur 200 is deviated from the side of the tibia, and faces the front side of the knee cap (in FIG. 2, the load portion 208 is a load portion for the medial condyle, and the load portion for the lateral condyle is not shown). Therefore, if the probe is applied from the front side of the knee cap, the ultrasonic beam can be applied at an angle close to perpendicular with respect to the surface of the load portion 208. In addition, it is also preferable to measure the cartilage around the load portion 208 for the purpose of comparison with the load portion 208, and, thus, the probe must be moved while being maintained at an orientation in which the ultrasound beam can be transmitted and received at an approximately perpendicular angle with respect to the cartilage.

In consideration of this, in the present embodiment, a support device of a probe is provided for realizing a movement of the ultrasonic probe suited for obtaining an ultrasound echo of the inside of the knee including the load portion of the cartilage on the distal end of the femur in a state where the knee is significantly bent such as when the person is sitting on a chair.

Figure 3:
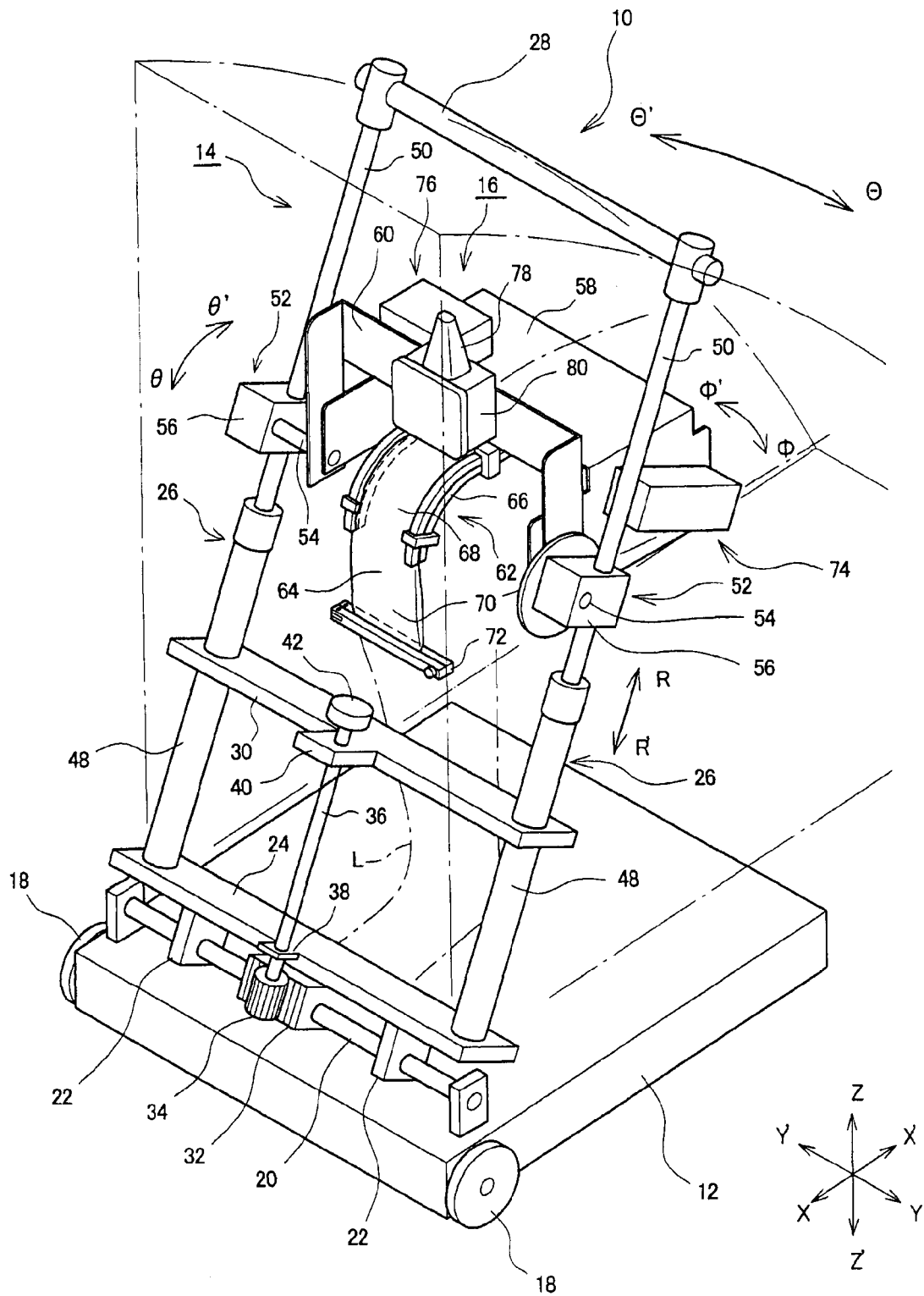
FIG. 3 is a perspective view showing the structure of primary portions of an ultrasonic probe support device 10.
Figure 4:
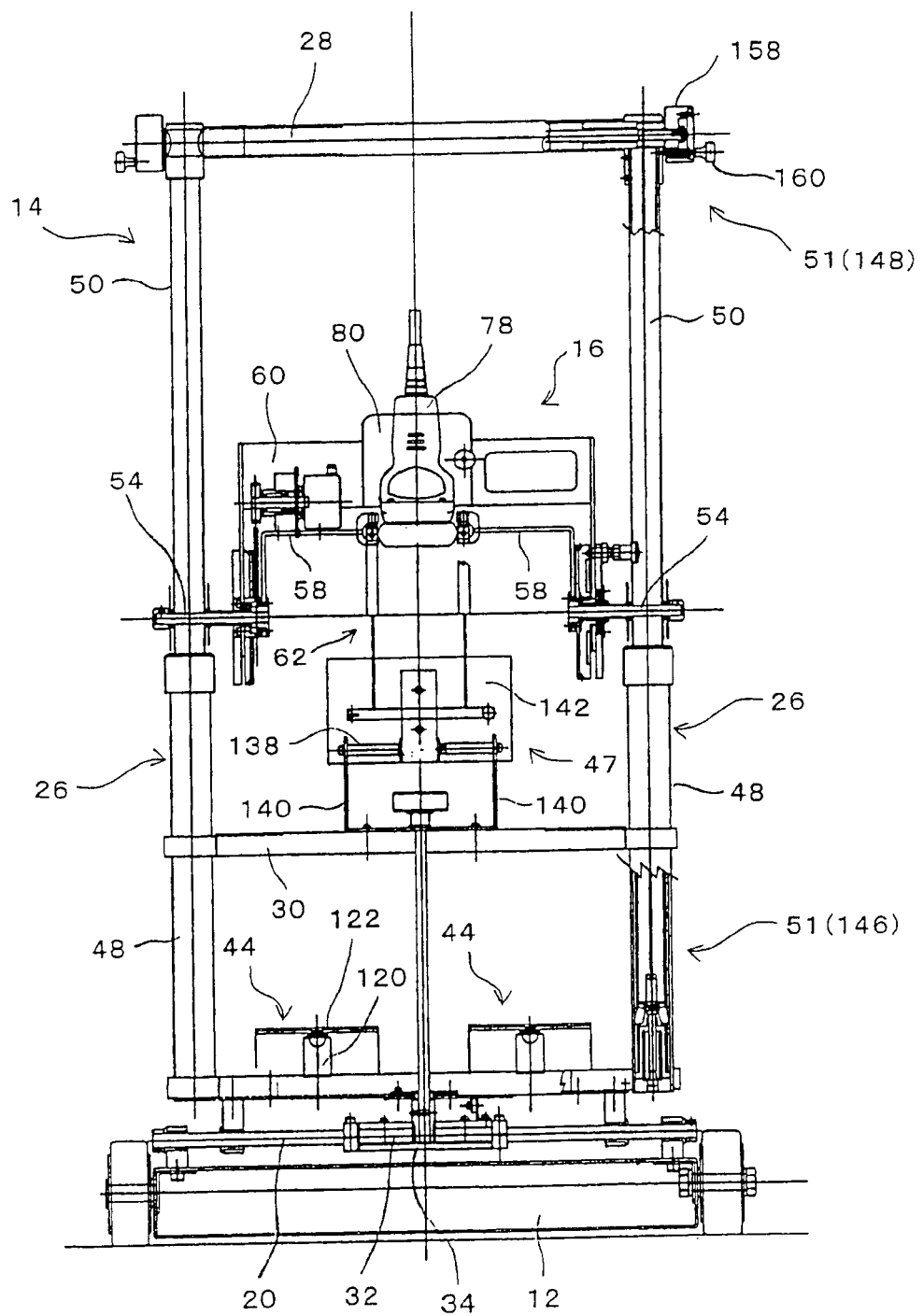
FIG. 4 is a front view of the ultrasonic probe support device 10.
Figure 5:
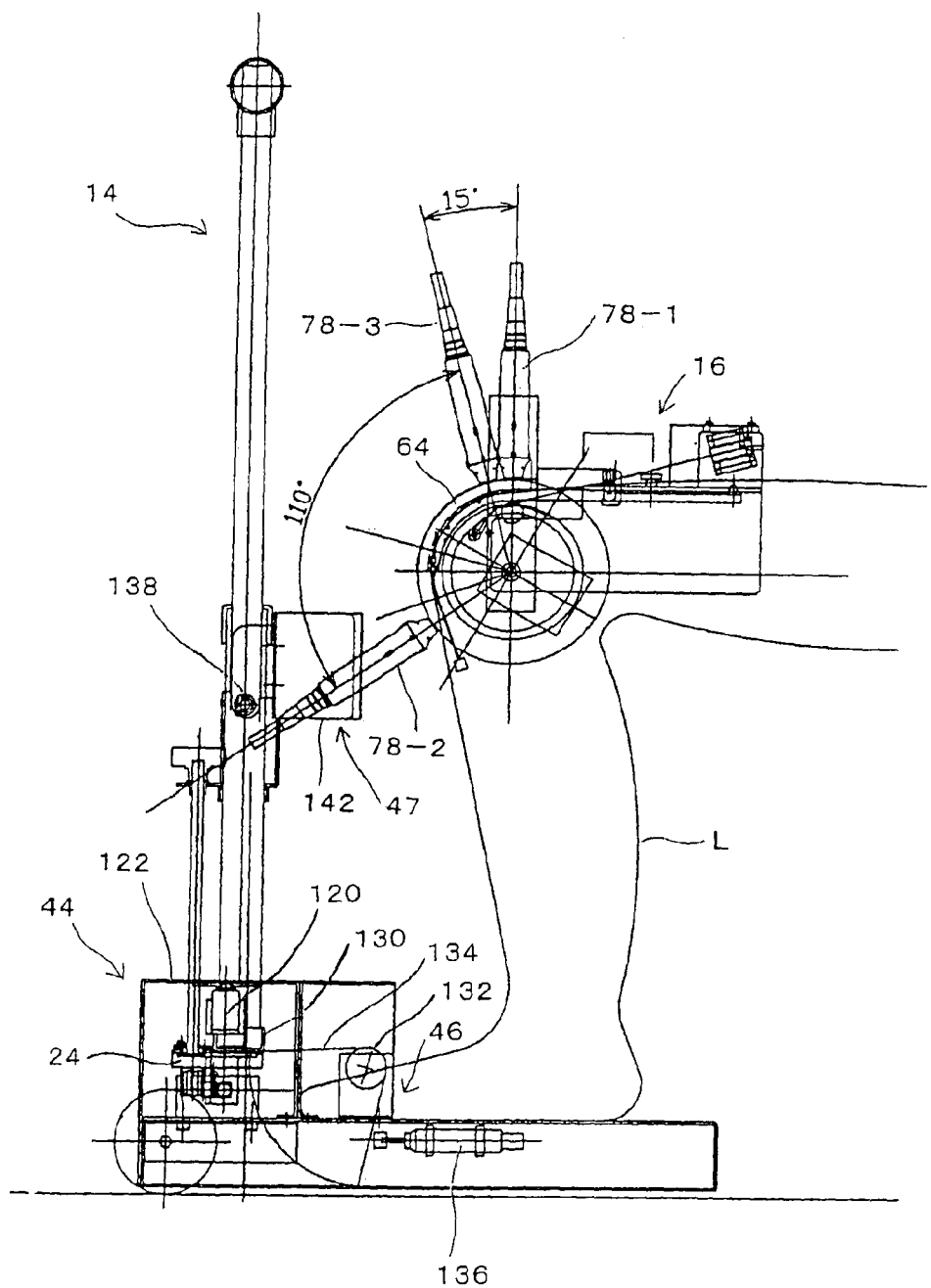
FIG. 5 is a side view of the ultrasonic probe support device 10.
Figure 6:
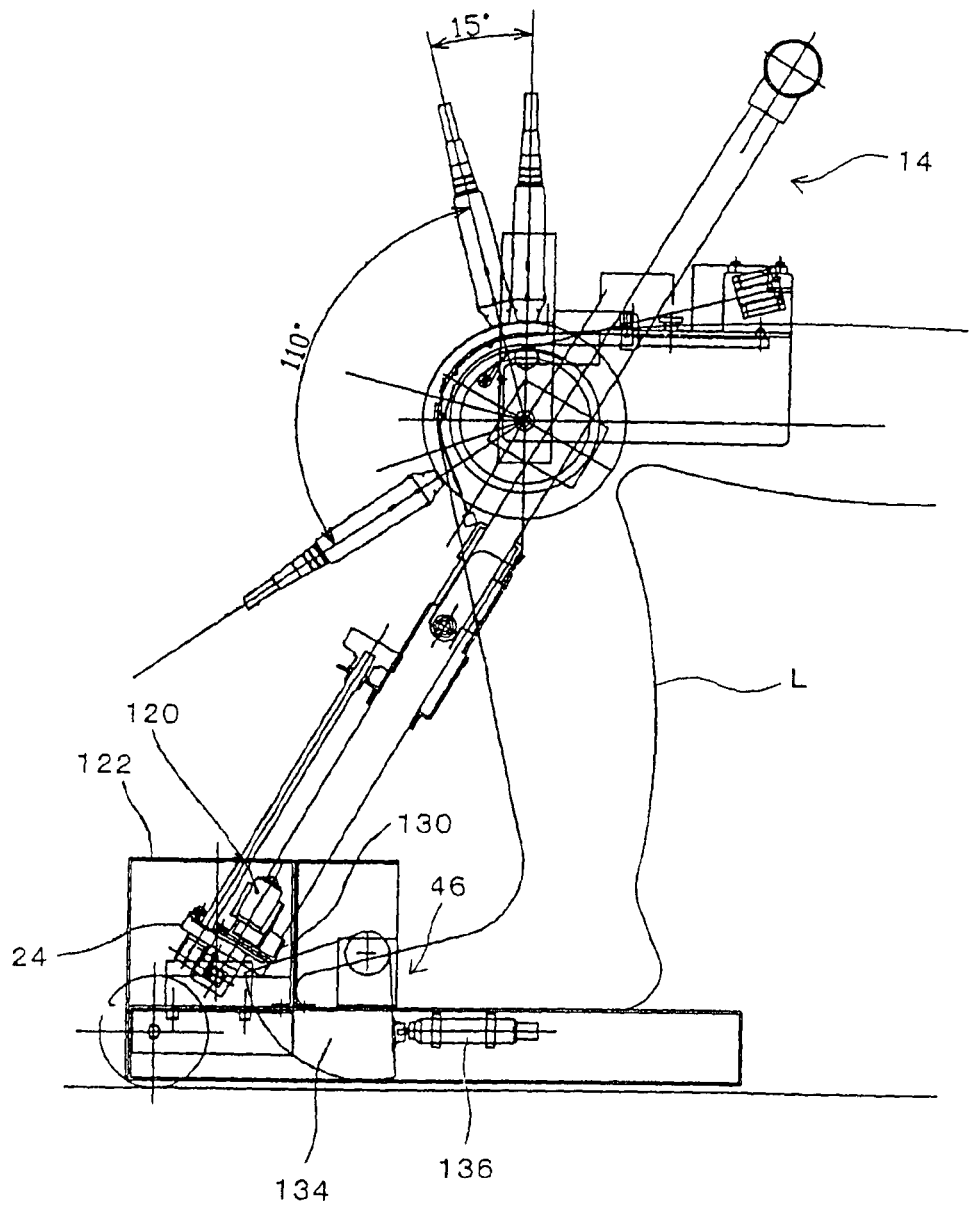
FIG. 6 is a side view of the ultrasonic probe support device 10.

A preferred embodiment of the present invention will now be described with reference to the drawings. FIGS. 3-6 are diagrams schematically showing the structure of an ultrasonic probe support device 10 according to the present embodiment. FIG. 3 is a perspective view, FIG. 4 is a front view, and FIGS. 5 and 6 are side views.

The ultrasonic probe support device 10 comprises a base 12 which is placed on a floor, a rotational frame 14 which is rotatably supported on the base 12, and a mounting unit 16 rotatably supported on the rotational frame 14. As shown with a reference sign symbol L in FIGS. 3, 5, and 6, an examinee places one of the left and right legs on the base 12. In the following description, the left and right, up and down, and front and rear directions and orientation are described with reference to the orientation of the examinee when one leg is in the state shown by the reference symbol L in the figures. More specifically, the X-X' direction in FIG. 3 is referred to as the front and rear direction, the Y-Y' direction is referred to as the left and right direction, and Z-Z' is referred to as the up and down direction. The respective directions are defined such that the orientation X is front, the orientation Y is left, and the orientation Z is up. In addition, in the state where the examinee sits with the two legs aligned with each other, the shin and thigh are approximately present in a sagittal plane (plane parallel to the median plane) passing through the center of the knee. In the following description, for the sake of explanation, regardless of the orientation of the median plane, the plane formed by the shin and the thigh when the knee is bent is described as the sagittal plane.

The base 12 has an approximate rectangular plate shape, is placed on a floor, and comprises a pair of casters 18 at a front end. When the support device 10 is moved, a rear end of the base 12 is lifted so that only the casters 18 contact the floor. At a region near the front edge of the base 12, a rotational frame support shaft 20 which extends in the left and right direction and which rotatably supports the rotational frame 14 is provided.

The rotational frame 14 comprises a lower lateral member 24 having two bearings 22 which engage the rotational frame support shaft 20, left and right radial members 26 which extend in a radial direction of the rotational movement, and an upper lateral member 28 which connects the left and right radial members 26 at the tips of the left and right radial members 26. An auxiliary lateral member 30 is provided between the upper and lower lateral members 24 and 28, bridging the left and right radial members 26. The rotational frame 14 has an overall ladder-like shape.

The bearing 22 engages the support shaft 20 such that the rotational frame 14 is rotatable about the support shaft 20 and moveable in a direction along the support shaft 20. The rotational direction around the support shaft 20 will hereinafter referred to as the Θ-Θ' direction, and the direction when the rotational frame is tilted in the downward direction will hereinafter referred to as Θ. A rack 32 is fixed on the support shaft 20, and a pinion 34 which engages the rack 32 is placed on the rotational frame 14. The pinion 34 is fixed at a lower end of a pinion shaft 36, and the pinion shaft 36 is held by pinion shaft holding portions 38 and 40 which are integrally or fixedly provided on the lower lateral member 24 and the auxiliary lateral member 30, respectively. A knob 42 is fixed at an upper end of the pinion shaft 36. When the knob 42 is rotated, the pinion 34 is integrally rotated, and the entire rotational frame 14 is moved in the Y-Y' direction.

The rotational frame 14 is tilted in the downward direction from a standing-straight position shown in FIG. 5, is rotated in the Θ direction as shown in FIG. 3 or 6, and is allowed to be positioned in an inclined position. A standing-straight orientation maintaining mechanism 44 for maintaining the rotational frame 14 in a standing-straight orientation is provided on the base 12 and the rotational frame 14 (refer to FIGS. 4 and 5). In addition, a damper mechanism 46 which limits the speed of tilt when the rotational frame 14 is inclined in the Θ direction is further provided on the base 12 (refer to FIGS. 5 and 6). Moreover, a left-and-right direction positioning mechanism 47 which determines the position in the left and right direction by contacting a recess having a V-shape or a U-shape on the shin of the examinee is provided on the rotational frame 14. In FIG. 3, for the sake of simplicity, the standing-straight orientation maintaining mechanism 44, the damper mechanism 46, and the left-and-right direction positioning mechanism 47 are not shown, and detailed description of these elements will be given later.

The radial member 26 of the rotational frame 14 has an extension/contraction function in an R-R' direction shown in the figures. The orientation R is the direction of extension of the radial member. The extension/contraction function is realized by forming the radial member 26 with two lower rods 48 and two upper rods 50 in a nested structure. In other words, the upper rod 50 enters the inside of the lower rod 48 and the upper rod 50 moves out from the inside of the lower rod 48, to achieve contraction and extension of the radial member 26. An extension/contraction lock mechanism 51 (refer to FIG. 4) for locking at a predetermined extension/contraction position is built in the rotational frame 14. The auxiliary lateral member 30 may be fixed on either of the upper and lower rods 48 and 50. In the present embodiment, in order to simplify the structure such that the extension/contraction of the pinion shaft 36 does not need to be considered, the auxiliary lateral member 30 is fixed on the lower rod 48. With the radial member 26 having the extension/contraction function, the rotational frame 14 extends/contracts with sliding of the two upper and lower frames. With this extension/contraction, a distance between a position for supporting the mounting frame 16 and the rotational frame support shaft 20 can be varied.

A mounting unit support portion 52 for supporting the mounting unit 16 is fixed on the upper frame of the rotational frame 14; more specifically, the upper rod 50. The mounting unit support portion 52 comprises a mounting unit support shaft 54 which rotatably supports the mounting unit 16, and a mounting unit support block 56 which connects the mounting unit support shaft 54 and the upper rod 50.

The mounting unit 16 comprises a mounting unit frame 58, a probe support frame 60, and a knee-contacting portion 62. For the purpose of simplifying the structure, in the present embodiment, both the mounting unit frame 58 and the probe support frame 60 are rotatably supported on the mounting unit support shaft 54. However, these shafts are not necessarily common, and the probe support frame may be rotatably supported by another shaft provided on the mounting unit frame 58. In addition, the shaft is typically parallel to the mounting unit support shaft 54. The rotational direction of the mounting unit frame 58 about the support shaft 54 is set as φ-φ', and the orientation φ' is set as a direction where the mounting unit frame 58 moves toward the thigh of the examinee. Moreover, the rotational direction of the probe support frame 60 about the mounting unit support shaft 54 is set as Θ-Θ' and the orientation of the probe support frame 60 tilting toward the front is set as Θ.

The mounting unit frame 58 has a gate shape as viewed from the front side; that is, an angular C-shape opened toward the downward direction, and the mounting unit support shaft 54 is provided separately at the left and right such that the mounting unit support shaft 54 does not enter the space inside the angular C-shape. Because the leg of the examinee enters the inside of the angular C-shape, there is employed a configuration in which no shaft passes through the inner space of the angular C-shape.

Figure 9:
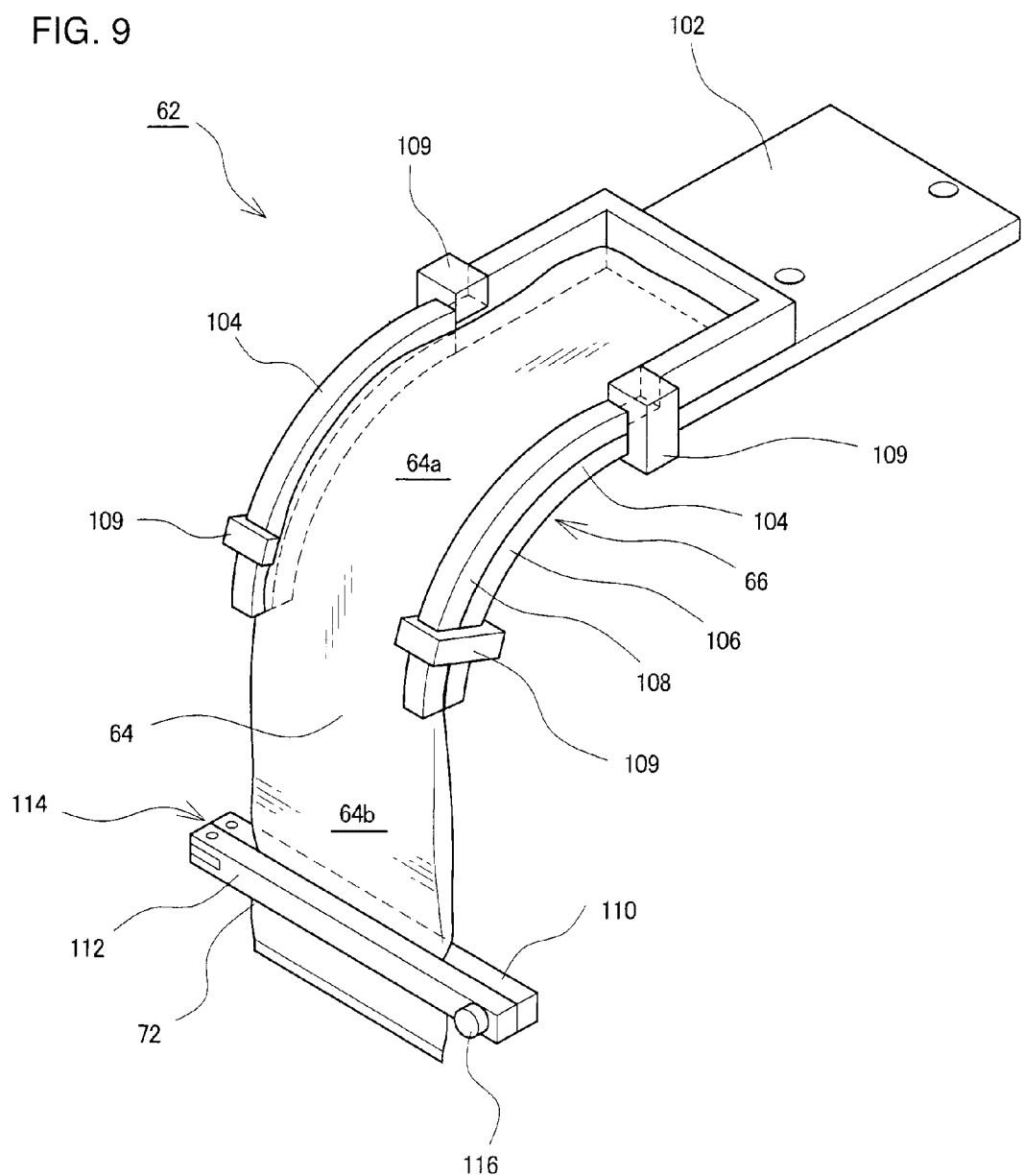
FIG. 9 is a perspective view showing a knee-contacting portion 62 serving as an acoustic matching device according to a preferred embodiment of the present invention.

As shown in FIG. 9, the knee-contacting portion 62 comprises an acoustic matching member 64 which extends from the mounting unit frame 58 to the front and is curved toward the downward direction. The acoustic matching member 64 is curved along the knee cap, and is in contact with the knee cap to position the mounting unit 16 in the front and rear direction. The acoustic matching member 64 is typically a rubber bag containing water (hereinafter referred to as "water bag 64"). When maintenance of the shape of the member cannot be expected, such as in the case of the water bag, a matching member support frame (water bag support frame) 66 for maintaining the above-described curved shape and supporting the curved shape is provided. The water bag support frame 66 is fixed on the mounting unit frame 58, and comprises a portion which is curved and which extends to the left and right sides of the knee when the mounting unit 16 is mounted on the leg of the examinee. The water bag 64 supported on the left and right by this portion of the water bag support frame 66 is maintained in the shape which is curved according to the shape of the water bag support frame 66. The water bag 64 comprises a free portion 64b which is a portion which is not supported on the left and right and which can move in the front and rear direction, at the tip of a fixed portion 64a having its left and right sides supported by the water bag support frame; that is, at a distal side of the leg. A distal side frame 72 for setting the shape of the end of the water bag 64 is provided at an end of the free portion 64b; that is, an end of the water bag 64. The water bag 64 is maintained in the curved plate shape by the water bag support frame 66 and the distal side frame 72.

The mounting unit frame 58 is equipped with a probe-driving mechanism 74 which rotationally drives the probe support frame 60, and a probe angle measuring mechanism 76 which measures an angle of the probe. Details of these mechanisms will be described later.

Similar to the mounting unit frame 58, the probe support frame 60 has an angular C-shape opened to the downward direction viewed from the front side. A probe holder 80 which detachably holds an ultrasonic probe 78 is fixed on the vertical portion of the angular C-shape; that is, the beam portion of the gate shape. The probe support frame 60 can be rotated independently from the mounting unit frame 58, and, with the rotational operation, a movement of the ultrasonic probe 78 along the knee cap is achieved. The ultrasonic probe 78 may be of a linear type, and is supported by the probe holder 80 such that the scanning plane is a plane orthogonal to the XY plane.

Figure 7:
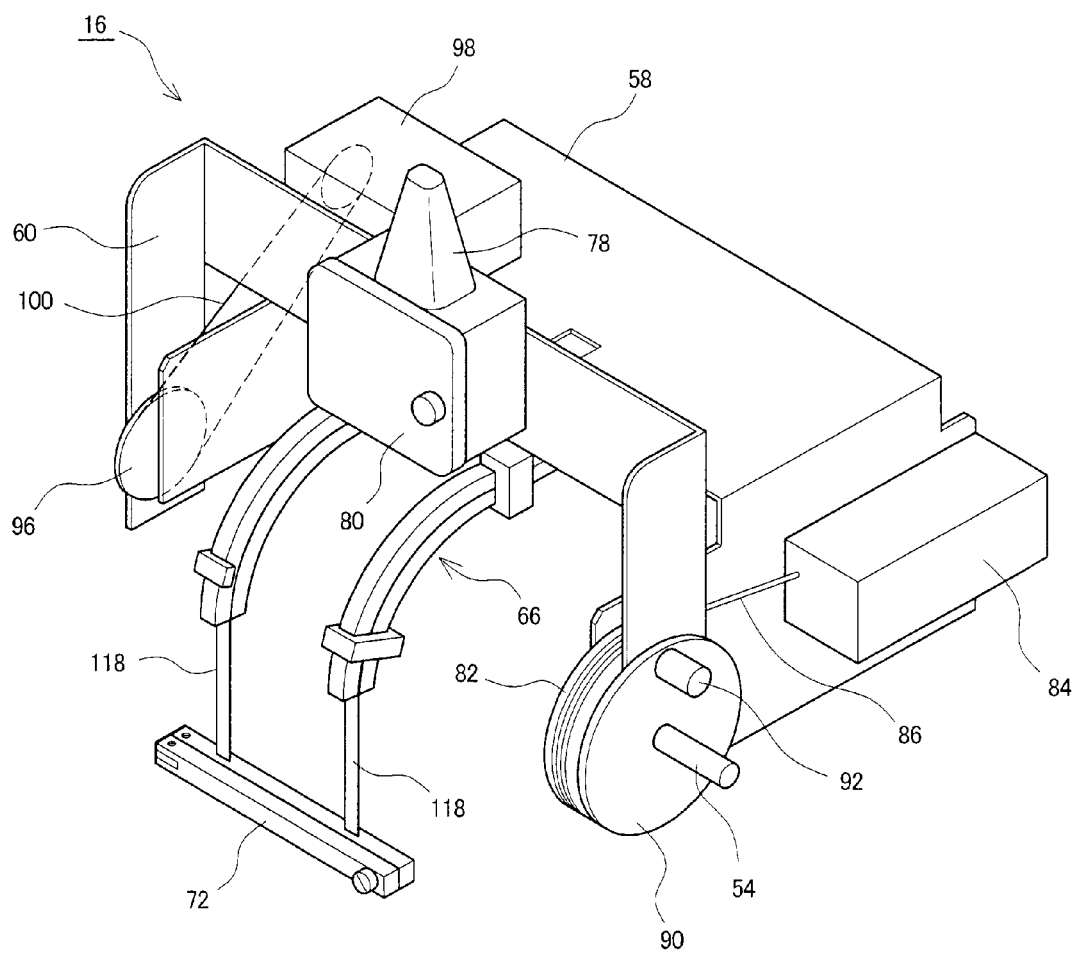
FIG. 7 is a perspective view schematically showing a structure of a mounting unit 16.
Figure 8:
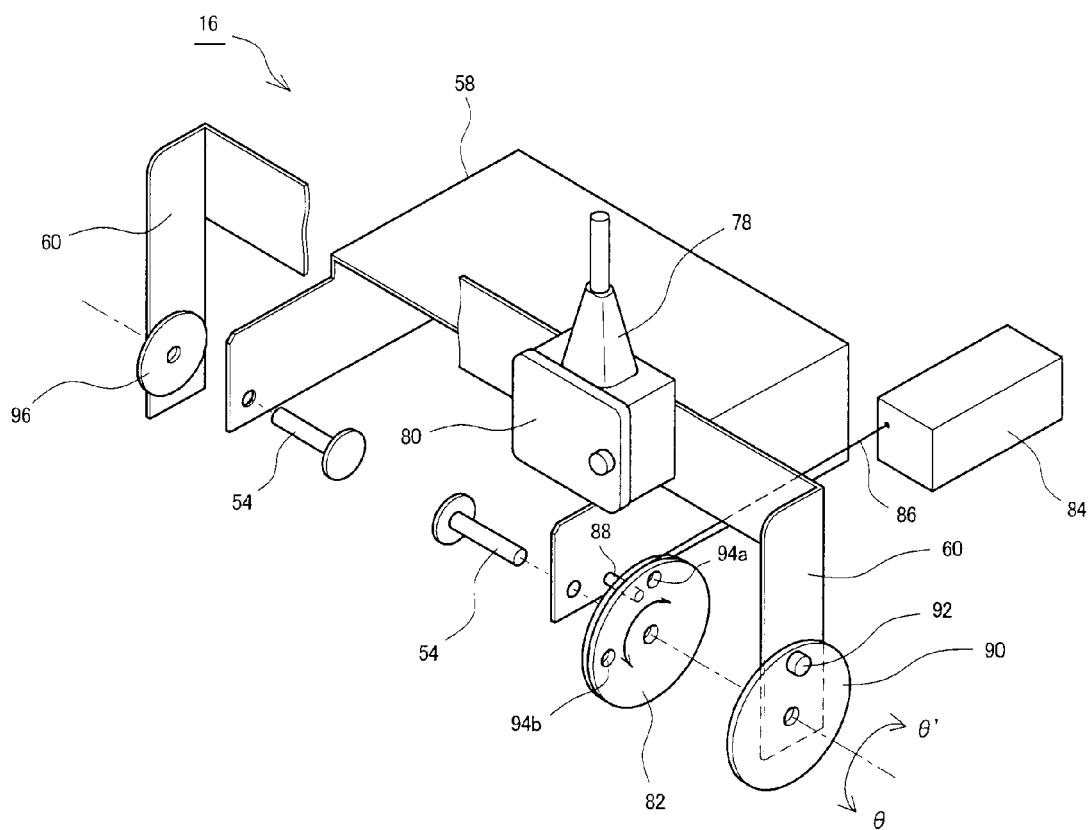
FIG. 8 is an exploded perspective view of the mounting unit 16.

FIG. 7 is an enlarged perspective view of the mounting unit 16, and FIG. 8 is an exploded perspective view of the mounting unit frame 58 and the probe support frame 60. As described above, the mounting unit frame 58 and the probe support frame 60 are rotatably supported in an independent manner on the mounting unit support shaft 54. In addition, a drive drum 82 is rotatably supported on the mounting unit support shaft 54. A wire 86 connected to a drive source 84 is wound around an outer periphery of the drive drum 82. The drive source 84 applies a tension force to the wire 86 in a direction of winding the wire 86. A stopper pin 88 is provided on the drive drum 82, and the pin 88 contacts the mounting unit frame 58 to form a rotation stopper of the drive drum 82 in the θ direction. A connecting plate 90 is fixed on the probe support frame 60, and these members are integrally rotated about the supporting shaft 54. An index plunger 92 is provided on the connecting plate 90. The index plunger comprises a plunger rod which extends through the connecting plate 90 and toward the back side, and can be maintained at a state where the rod is projected to the back side and a state where the rod is withdrawn. Two index holes 94a and 94b are formed in the drive drum 82 to which the projected plunger rod is inserted. In a state where the plunger rod projects and is engaged with one of the index holes 94a and 94b, the drive drum 82, the connecting plate 90, and the probe support frame 60 are integrally rotated. In the state where the plunger rod is withdrawn, the drive drum 82 and the connecting plate 90 can be independently rotated.

The index hole 94a is formed at a position where, when the stopper pin 88 is at a position of contact with the mounting unit frame (hereinafter simply referred to as "reference position of the drive drum"), if the plunger rod is inserted into the hole 94a and is engaged, the probe support frame 60 is set in a vertical orientation. In this process, the ultrasonic probe 78 is also at the vertical position and in a standing-straight state. This position of the ultrasonic probe 78 is defined as θ=0°. The other index hole 94b is formed at a position where, when the drive drum 82 is at its reference position, if the index rod is inserted and is engaged, the probe support frame 60 and the ultrasonic probe 78 are set to a position tilted by 90° to the front (θ=90°).

When the probe support frame is tilted to the front while the rod of the index plunger 92 is engaged to the index hole 94a, the wire 86 is unreeled from the drive source 84 due to the rotation of the drive drum 82. A tension force is applied to the wire 86 by the drive source 84, and, when the force for tilting to the front direction is released, the drive drum 82 is driven in the orientation θ' by the tension force. With this process, the ultrasonic probe also returns toward θ=0°. The drive source 84 preferably rotates the drive drum 82 at a constant speed.

In addition, an encoder drum 96 is fixed on the probe support frame 60 coaxially with the mounting unit support shaft 54. A belt 100 is wound around a rotary encoder 98 equipped on the encoder drum 96 and the mounting unit frame 58. The rotary encoder 98 detects a rotational angle of the probe support frame 60; that is, a rotational angle of the ultrasound probe. In the present embodiment, the drive drum 82 and the encoder drum 96 are separately placed on the left and right of the mounting unit frame 58, but alternatively, both drums may be placed at one of the left and right sides.

FIG. 9 is a diagram showing details of the knee-contacting portion 62. The knee-contacting portion 62 comprises the water bag 64 functioning as the acoustic matching member, and functions as an acoustic matching device which is fitted on the knee and achieves acoustic matching between the ultrasonic probe which moves along the knee cap and the knee. The support frame 66 comprises a base portion 102 fixed on the mounting unit frame 58, and two arm portions 104 which extend from the base portion 102 to the front and which are curved toward the downward direction. The base portion 102 and two arm portions 104 form an approximate angular C-shape as an overall shape. The curved portion of the arm portion 104 is an arc in the present embodiment, and a central angle assumed by the arc is 90°. The center of the arc is on a rotational axis of the probe support frame. The support frame is divided into an inner periphery side and an outer periphery side. An inner frame 106 on the inner periphery side and an outer frame 108 on the outer periphery side each have an approximate angular C-shape, and the inner frame 106 and the outer frame 108 are connected by four clips 109. The base portion 102 of the inner frame 106 extends toward the rear direction, where the inner frame 106 is fixed on the mounting unit frame 58 by a bolt or the like.

The water bag 64 which functions as the acoustic matching member is sandwiched and supported by the inner frame 106 and the outer frame 108. The water bag 64 has a proximal side of left and right edges sandwiched and supported by portions belonging to the arm portions of the inner and outer frames 106 and 108, and an edge of the proximal side sandwiched and supported by a portion belonging to the base portion. With this structure, the water bag 64 between the left and right arm portions 104 is set as the fixed portion 64a having an approximate rectangular cross section and maintained in the curved plate shape. The water bag 64 further extends to the portion beyond the arm portion 104; that is, toward the distal side, and is sandwiched by the distal end frame 72 at a position distanced from the arm portion 104. The distal end frame 72 closes and seals the opening of the water bag 64. The distal frame has a structure wherein two rod-shaped frames; that is, an inner frame 110 and an outer frame 112, are connected at one end with a hinge 114 and are fixed by the other end being fastened by a screw. The water bag 64 is sandwiched between the inner and outer frames 110 and 112, to seal the water inside the water bag.

The water bag 64 between the tip of the arm portion 104 and the distal end frame 72 forms the free portion 64b in which the shape is not fixed and which can swing in the front and rear direction in the manner of a pendulum. The distal end frame 72 may be constructed so as to be hung by the water bag 64. In addition, the distal end frame 72 may be hung and supported by a wire extending from tips of the two arm portions 104 or a thin plate-shaped flexible frame 118. FIG. 6 shows a thin plate-shaped member as an example of the flexible frame 118. The thin plate is placed such that the width direction of the plate is the left and right direction, and, with this thin plate, swinging of the free portion of the water bag 64 in the front and rear direction is secured. In addition, when a thin plate is employed, the swinging in the left and right direction can be inhibited.

In a state where the knee-contacting portion 62 is in contact with the knee, the ultrasonic probe 78 is moved in a tracing manner on a surface of an outer periphery of the water bag 64, and ultrasound information is obtained. The fixed portion 64a of the water bag contacts the knee cap and contributes to positioning in the front and rear direction of the mounting unit 16. In this configuration, because the fixed portion does not extend from the front to a region below the knee, the fixed portion does not obstruct mounting of the mounting unit 16. On the other hand, because of the flexibility of the free portion, during the measurement, the ultrasonic probe can be moved to a region further below the horizontal direction, and the ultrasound can be transmitted to and from a knee joint from a position of, for example, 35° below the horizontal direction. Alternatively, so long as the positioning function in the front and rear direction of the mounting unit 16 can be achieved, the fixed portion 64a of the water bag may have an angle assuming the center of the arc of the fixed portion being an angle less than 90°.

The knee-contacting portion 62 has both the function to position the mounting unit 16 in the front and rear direction and a function to achieve acoustic matching during transmission and reception of the ultrasound. Alternatively, the knee-contacting portion 62 may be configured to have only the positioning function. For example, a plate which contacts a region near a proximate end of a tibia below the knee may be fixed to the mounting unit frame 58 and the positioning of the front and rear direction may be achieved with this plate. In this case, the acoustic matching member is not provided on the mounting unit, and it is possible to apply an acoustic jelly or the like on the knee cap and execute the measurement.

Figure 10:
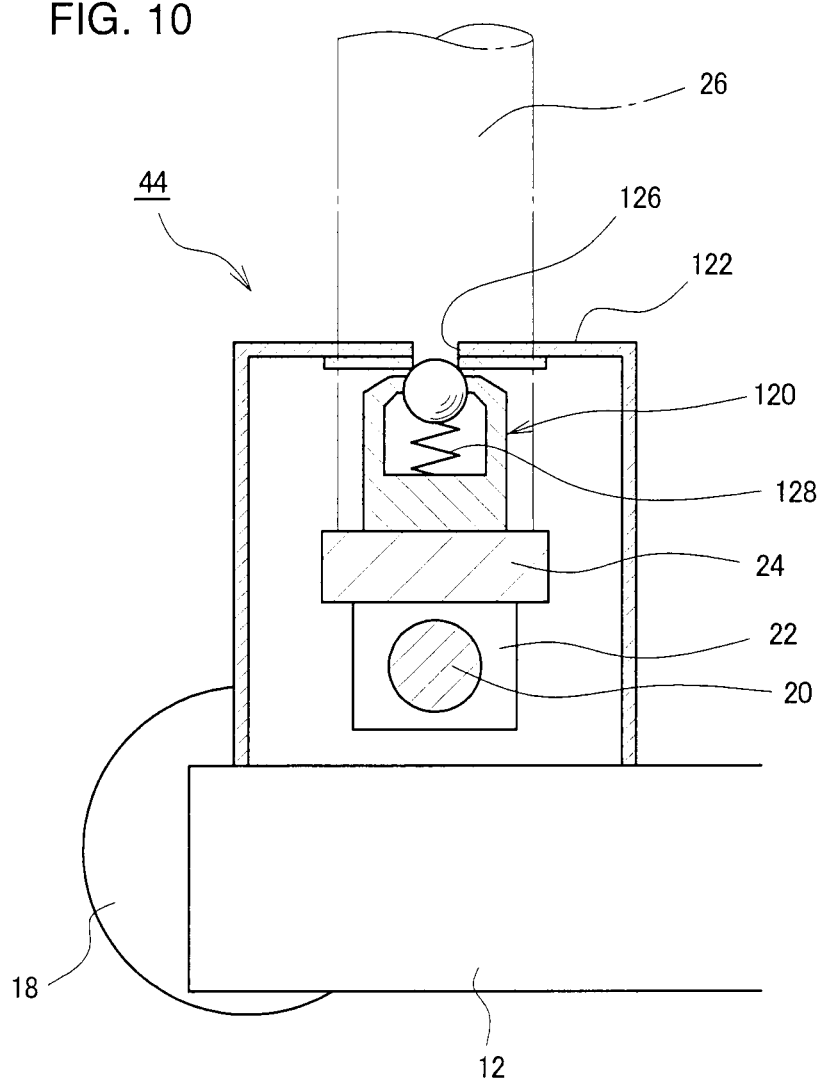
FIG. 10 is a schematic diagram schematically showing the structure of a standing-straight orientation maintaining mechanism 44.

FIG. 10 is a cross sectional diagram schematically showing a structure of the standing-straight orientation maintaining mechanism 44. The standing-straight orientation maintaining mechanism 44 comprises a ball plunger 120 which is fixedly provided on the lower lateral member 24, and a ball-receiving box 122 fixed on the base 12. A ball-receiving slit 126 which engages a ball 124 of the ball plunger is formed on an upper surface of the ball-receiving box 122. The ball-receiving slit 126 extends in a left and right direction; that is, a direction through the page of FIG. 10, so that, even when the rotational frame moves to the left and right, the engagement between the ball and the slit is achieved. The ball 124 is urged by a spring 128, the engagement between the ball and the slit is maintained, and, in this state, the rotational frame 14 is maintained in the standing-straight position. When the rotational frame 14 is moved in the tilting direction, the ball 124 is pressed into the plunger against the urging force of the spring 128, and the engagement between the slit and the ball is released (refer to FIG. 6).

FIGS. 5 and 6 show the damper mechanism 46 for inhibiting the speed of tilt of the rotational frame 14 and for carrying at least a part of its weight. A pressurizing member 130 is fixed on the lower lateral member 24, and a transfer plate 134 which rotates about a shaft 132 is in contact with the pressurizing member 130. The transfer plate 134 has an approximate fan shape, with the pressuring member 130 being in contact with one radius and a rod of a damper 136 in contact with the other radius. The damper 136 is stored in the base so that its axis is in the horizontal direction, and contributes to inhibition of the height of the base. When the rotational frame 14 is moved to tilt from the standing straight state (FIG. 5), the pressurizing member 130 pushes the transfer plate 134. Because of this process, the transfer plate 134 is rotated in the counterclockwise direction in the figure, and presses the rod of the damper 136. In this process, because of a resistance caused by the damper 136, the speed of tilt of the rotational frame 14 is inhibited. In addition, the damper applies an urging force via the transfer plate 134 so that the rotational frame 14 is rotated in a direction toward standing straight; that is, an orientation of $\Theta'$. Because of this, the weight of the rotational frame 14 and that of the mounting unit 16 are at least partially cancelled.

Figure 11:
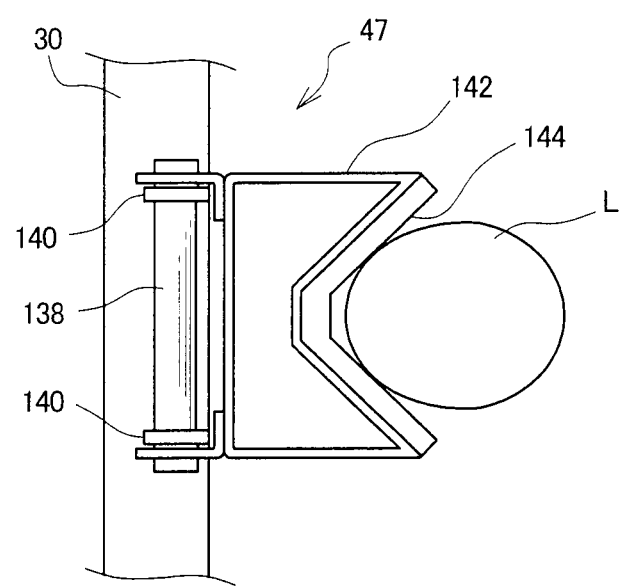
FIG. 11 is a schematic diagram schematically showing a structure of a left-and-right position determining mechanism 47.

FIGS. 4, 5, and 11 show the left-and-right direction positioning mechanism 47 which positions the rotational frame 14 in the left and right direction according to the legs of the examinee. FIG. 11 is a plan view schematically showing the left-and-right positioning mechanism 47. A bracket 140 for supporting a shaft 138 is fixed on the auxiliary lateral member 30. A contact block 142 which contacts the leg of the examinee; in particular, the shin, is supported in a rotatable manner on the shaft 138. The contact block 142 does not move in the left and right direction with respect to the rotational frame 14. As shown in FIG. 11, a concave portion with respect to the shin, typically a V-shape channel 144, is formed in the contact block 142. The rotational frame 14 is moved in the left and right direction such that the channel 144 contacts the shin and the position is adjusted such that the leg is positioned at the center of the rotational frame 14 in the left and right direction. The movement in the left and right direction is achieved by rotating the knob 42 as described above. In addition, by contacting the contact block 142 to the shin, it is possible to prevent a state where the shin is tilted drastically to the left or right when viewed from the front.

Figure 12:
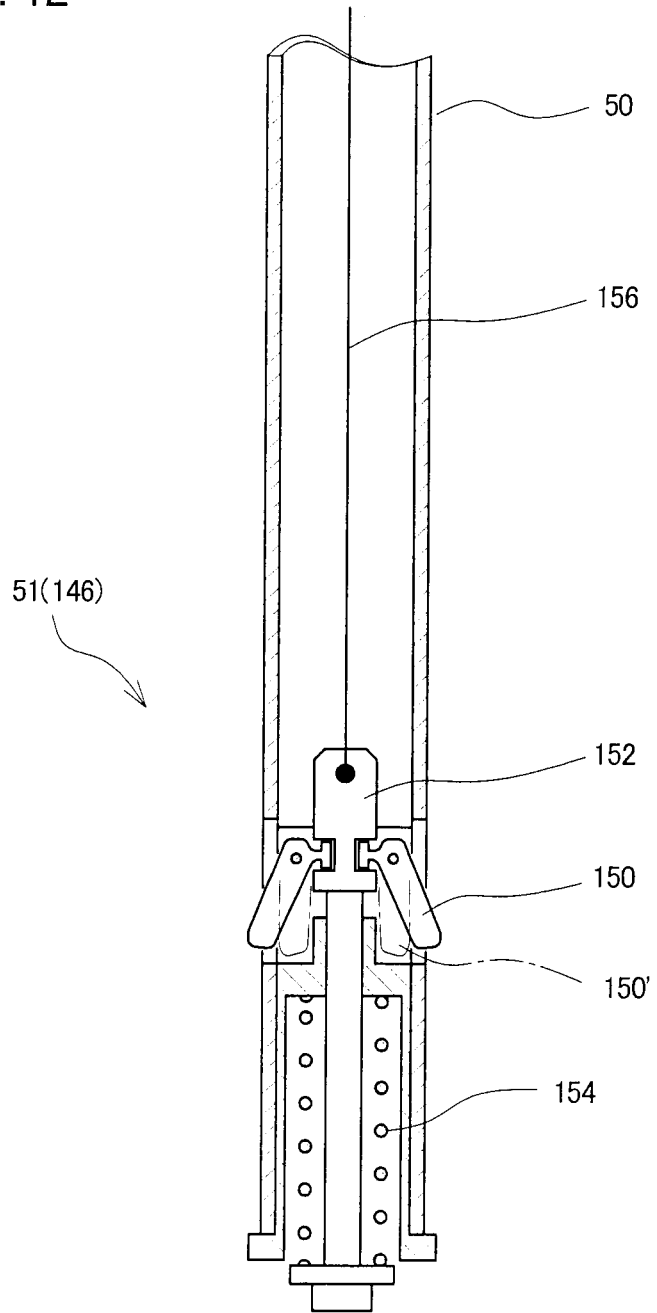
FIG. 12 a diagram showing a lock portion 146 of an extension/contraction lock mechanism 51.

As described above, the rotational frame 14 comprises the extension/contraction lock mechanism 51 which can be extended/contracted, and which fixes the position of the rotational frame 14. The extension/contraction lock mechanism 51 comprises a lock portion 146 provided on a lower end of the upper rod 50 which enters the inside of the lower rod 48 and a drive portion 148 provided at an end of the upper lateral member 28. FIG. 12 shows a detailed structure of the lock portion 146. The upper rod 50 is hollow, and comprises a pair of lock arms 150 which open and close inside the upper rod 50. A position indicated in the figure with reference numeral 150 represents an open state and a position indicated in the figure with reference numeral 150' represents a closed state. A connecting rod 152 is connected to the lock arm 150, and the lock arm 150 is opened and closed by upward and downward movements of the connecting rod 152. The connecting rod 152 is connected to a spring 154 at a lower end of the figure, and is constantly urged in the downward direction by the spring 154. A wire 156 which extends in the upper rod 50 in the upward direction is connected to the upper end of the connecting rod 152. The wire 156 extends to the upper end of the upper rod 50 and reaches the inside of the upper lateral member 28. A lock knob 158 is provided on the end of the upper lateral member 28, and an end of the wire 156 is connected to a cylindrical portion of the lock knob 158 extending inside the upper lateral member 28. A plunger 160 is provided on the lock knob 158, and is pressurized toward the upper rod 50 with a spring. Because of this structure, when a tip of the plunger 160 enters a hole formed in the upper rod 50, the rotation of the lock knob 158 can be stopped.

Normally, the lock arm 150 is maintained in the open state because the connecting rod 152 is urged in the downward direction by the spring. In this process, the tip of the lock arm 150 protrudes from the outer peripheral surface of the upper rod 50, contacts the inner peripheral surface of the lower rod 48 which is in a nested structure with the upper rod 50, and locks the upper and lower rods by friction. When the lock knob 158 is rotated and the wire 156 is wound around the cylindrical portion thereof, the connecting rod 152 is pulled by the wire and moves upward against the urging force of the spring 154, and the lock arm 150 is closed. With this structure, the engagement of the tip of the lock arm 150 with the inner peripheral surface of the lower rod 48 is released, and the upper and lower rods are set in a slidable state. After the upper and lower rods 50 and 48 are slid and the length of the rotational frame 14 is set to a suitable length, the lock knob 158 is rotated in a reverse direction to loosen the tension force applied to the wire 156 and open the lock arm 150. With this process, the upper and lower rods are again locked.

Figure 13:
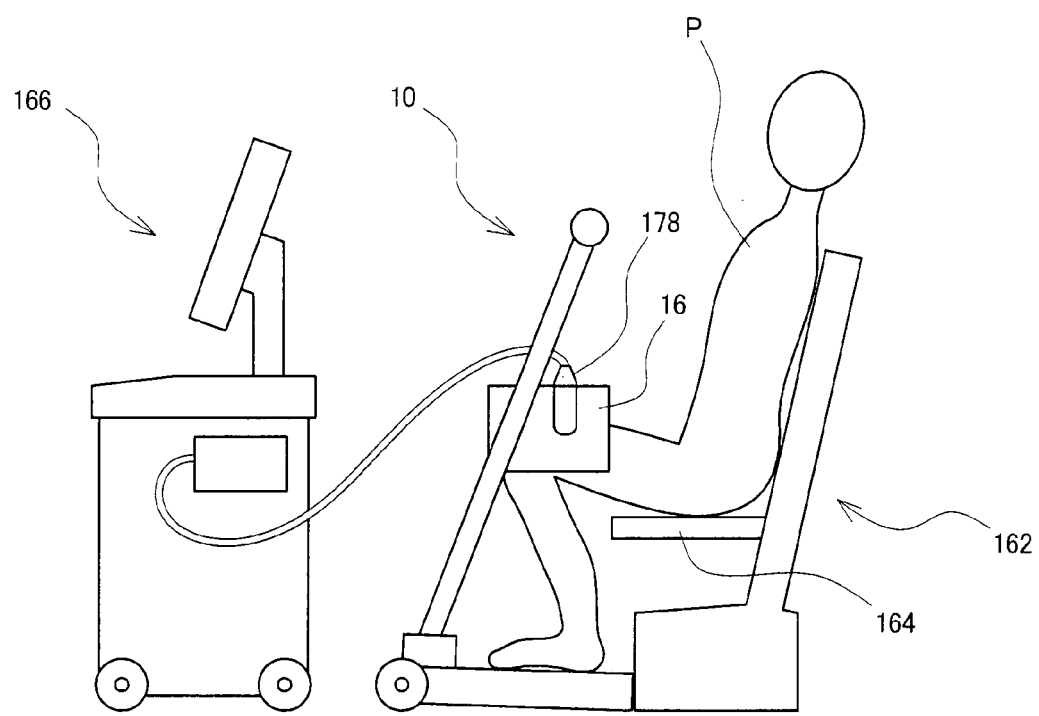
FIG. 13 is a schematic diagram of a system for diagnosing cartilage of a knee joint.

FIG. 13 is a diagram showing a system summary of an ultrasonic probe support device and an ultrasound diagnosis apparatus for diagnosing the cartilage of the knee joint; in particular, the cartilage at a distal end of the femur. An examinee P sits on a chair 162, in a state where the knee is bent. A sitting surface 164 of the chair 162 can be moved up and down so that the height can be adjusted to achieve a suitable orientation of the examinee for observation of the cartilage of the knee joint. The figure shows a state where the mounting unit 16 of the ultrasonic probe support device 10 described above is mounted on the knee of the examinee P. The ultrasonic probe 178 is connected to an ultrasound diagnosis apparatus 166. The ultrasound diagnosis apparatus 166 is a well-known apparatus, and will not be described here.

An actual operation during the measurement will now be described. In an initial state, as shown in FIG. 5, the rotational frame 14 is in a standing straight state. In FIG. 5, the mounting unit 16 is shown not in the initial state, but in a position of mounting, for the purpose of later description. After the examinee P sits on the chair 162, the leg is placed on the base such that the thighs are approximately parallel to each other and the saggital plane is approximately parallel to the front and rear axis (X-X' axis) of the device. The knob 42 is rotated to roughly position the rotational frame 14 in the left and right direction by visual observation. The rotational frame 14 is tilted in the orientation Θ and extended in the orientation R, the mounting unit frame 58 is placed on the upper surface of the thigh, and the knee-contacting portion 62 is contacted with the knee cap. With this process, the mounting unit 16 is positioned in the up and down direction and the front and rear direction. In addition, the knob 42 is adjusted and the position in the left and right direction is determined so that the shin enters without being contacted with the channel 144 of the contact block 142. FIG. 6 shows a state where the rotational frame 14 is tilted. In FIG. 6, however, the left-and-right positioning mechanism 47 is not shown.

The index plunger 92 is operated to release the connection between the connecting plate 90 and the drive drum 82, so that the probe support frame 60 can be manually moved. The operator manually moves the probe support frame 60 and checks whether or not desired ultrasonic echo information can be obtained while viewing the monitor of the ultrasound diagnosis apparatus 166. If there is no problem, the index plunger 92 is engaged with the index hole 94a, to achieve a standing straight position of the ultrasonic probe 78. The probe in this state is indicated in FIG. 5 with reference numeral 78-1. The operator manually rotates the probe support frame 60 in the orientation θ, and moves the probe to the position of a reference numeral 78-2 in FIG. 5. This position is a position which is 35° further in the downward direction from the horizontal direction. As described above, the free portion 64b which can swing in the front and rear direction is provided at the distal side of the water bag 64. The free portion is pushed by the ultrasonic probe 78-2 moved to a region below the knee and swings to the rear direction, and closely contacts a region below the knee or above the shin.

With the rotation of the probe support frame 60 in the orientation θ, the drive drum 82 is also rotated, and the wire 86 is unreeled from the drive source 84. When the probe support frame 60 is released, the probe support frame 60 is rotated in the orientation θ' by the tension force from the drive source 84. The ultrasonic probe 78 moves along an arc of the saggital plane passing through the center of the knee and while maintaining a state of being directed toward the center of the arc. The center of the arc of the trajectory of the ultrasonic probe approximately matches the mechanical center of the knee joint. A radius of the trajectory (arc) of movement of the probe tip is preferably 40 mm~60 mm plus the thickness of the water bag 64, and, in the present embodiment, is set to 70 mm because the thickness of the water bag is 10 mm~20 mm. The center of the arc of the trajectory of the ultrasonic probe approximately matches the mechanical center of the knee joint. In addition, in order to achieve an approximate constant movement speed of the ultrasonic probe, the tension force generated by the drive source 84 is approximately constant. Moreover, the ultrasonic probe 78 moves constantly in contact with the surface of the water bag 64, tracing the surface of the water bag 64. While the frame 60 is rotated, the rotational angle is detected by the rotary encoder 98. Echo information of the ultrasound is obtained for each predetermined angle, and the information is stored in the storage of the ultrasound diagnosis apparatus 166. With this process, mechanical scanning of the ultrasound; in particular, concave scanning, is realized. The scanning direction of the concave scanning and the scanning surface of the ultrasonic probe 78 which is of the linear type are orthogonal to each other, and, thus, three-dimensional information of the knee joint can be obtained. When the probe is tilted from the standing straight position to a position of 15° to the front (which is indicated with a reference numeral 78-3), the measurement is completed. Afterwards, the probe support frame 60 is rotated to the standing straight position (78-1). When the rotation of the ultrasonic probe is completed, the rotational frame 14 is moved to the standing straight position, the lock of the extension/contraction lock mechanism 51 is released, and the rotational frame 14 is contracted. With the rotational frame 14 being contracted, the ease of storage of the supporting device 10 can be improved.

EXPLANATION OF REFERENCE NUMERALS

10 ULTRASONIC PROBE SUPPORT DEVICE; 14 ROTATIONAL FRAME; 16 MOUNTING UNIT; 54 MOUNTING UNIT SUPPORT SHAFT; 58 MOUNTING UNIT FRAME; 60 PROBE SUPPORT FRAME; 62 KNEE-CONTACTING PORTION (ACOUSTIC MATCHING DEVICE); 64 ACOUSTIC MATCHING MEMBER (WATER BAG); 64a FIXED PORTION; 64b FREE PORTION; 66 WATER BAG SUPPORT FRAME; 72 DISTAL SIDE FRAME; 78

ULTRASONIC PROBE; 82 DRIVE DRUM; 86 WIRE; 90 CONNECTING PLATE; 162 CHAIR; 166 ULTRASOUND DIAGNOSIS APPARATUS

The invention claimed is:

1. An acoustic matching device for a knee for an ultrasonic probe and which is mounted on a knee cap of a bent knee, the acoustic matching device for knee comprising:
   a water bag containing water; and
   a water bag support frame which sandwiches and supports the water bag at a left side and a right side of the knee and which is curved along the knee cap, wherein
   the water bag has a plate shape which is curved according to the shape of the water bag support frame, and
   wherein the water bag comprises a fixed portion having a side supported by the water bag support frame, and a free portion which extends from the fixed portion toward a distal side and which is allowed to move in a front and rear direction of the knee.

2. The acoustic matching device for knee according to claim 1, further comprising
   a distal side frame which sandwiches an edge of the free portion on a distal side and which extends in a left and right direction.

3. The acoustic matching device for knee according to claim 1, further comprising:
   a flexible frame having a thin plate shape, which extends from the water bag support frame toward a distal side and which is connected to the distal side frame, wherein
   the flexible frame has a width direction of the thin plate as the left and right direction, and is deflected to restrict movement of the distal side frame in the left and right direction while allowing movement of the distal side frame in the front and rear direction.

* * * * *